United States Patent
Robie et al.

(10) Patent No.: US 7,153,304 B2
(45) Date of Patent: Dec. 26, 2006

(54) INSTRUMENT SYSTEM FOR PREPARING A DISC SPACE BETWEEN ADJACENT VERTEBRAL BODIES TO RECEIVE A REPAIR DEVICE

(75) Inventors: Bruce Robie, Glen Rock, NJ (US); Felix Blouin, Sterling Forest, NY (US); Rafael Zubok, Midland Park, NJ (US); John Wilhelmy, Danville, CA (US)

(73) Assignee: Zimmer Trabecular Metal Technology, Inc., Allendale, NJ (US)

( * ) Notice: Subject to any disclaimer, the term of this patent is extended or adjusted under 35 U.S.C. 154(b) by 490 days.

(21) Appl. No.: 10/035,863

(22) Filed: Dec. 31, 2001

(65) Prior Publication Data

US 2002/0161366 A1    Oct. 31, 2002

Related U.S. Application Data

(60) Provisional application No. 60/259,262, filed on Dec. 29, 2000.

(51) Int. Cl.
*A61B 17/58* (2006.01)
(52) U.S. Cl. .................. 606/90; 606/61; 623/17.11
(58) Field of Classification Search .................. 606/90, 606/60, 61, 79, 57, 105, 99, 96, 84; 623/17.11, 623/17.16; 621/17.11
See application file for complete search history.

(56) References Cited

U.S. PATENT DOCUMENTS

| | | | |
|---|---|---|---|
| 4,501,269 A | | 2/1985 | Bagby |
| 4,878,915 A | | 11/1989 | Brantigan |
| 5,015,247 A | | 5/1991 | Michelson |
| 5,026,373 A | | 6/1991 | Ray et al. |
| 5,055,104 A | | 10/1991 | Ray |
| 5,308,350 A | * | 5/1994 | Mikhail ........................ 606/88 |
| 5,484,437 A | * | 1/1996 | Michelson .................... 606/61 |
| 5,505,732 A | | 4/1996 | Michelson |
| 5,722,977 A | * | 3/1998 | Wilhelmy ..................... 606/84 |
| 5,797,909 A | | 8/1998 | Michelson |
| 5,947,971 A | * | 9/1999 | Kuslich et al. ................ 606/80 |
| 5,993,453 A | | 11/1999 | Bullara et al. |
| 6,030,390 A | * | 2/2000 | Mehdizadeh .................. 606/84 |
| 6,042,582 A | | 3/2000 | Ray |
| 6,059,790 A | | 5/2000 | Sand et al. |
| 6,063,088 A | | 5/2000 | Winslow |
| 6,080,155 A | | 6/2000 | Michelson |
| 6,096,038 A | | 8/2000 | Michelson |
| 6,113,602 A | | 9/2000 | Sand |
| 6,210,412 B1 | * | 4/2001 | Michelson .................... 606/61 |
| 6,224,599 B1 | * | 5/2001 | Baynham et al. .............. 606/61 |
| 6,440,139 B1 | * | 8/2002 | Michelson .................... 606/80 |
| 6,589,247 B1 | * | 7/2003 | McGahan et al. ............. 606/90 |
| 6,648,895 B1 | * | 11/2003 | Burkus et al. ................. 606/90 |
| 6,824,565 B1 | * | 11/2004 | Muhanna et al. ......... 623/17.16 |

* cited by examiner

*Primary Examiner*—Pedro Philogene
(74) *Attorney, Agent, or Firm*—Duane Morris LLP (57) ABSTRACT

An instrument system for preparing a disc space between adjacent vertebral bodies to receive a repair device includes a series of distractors for distracting the vertebral bodies in a manner that restores natural lordosis of the lumbar and cervical spine, a vertebrae immobilizing template to fix the positions of the bodies, a handle for employing the distractor and the template, and a reamer for cutting tissue from endplates of the vertebral bodies.

29 Claims, 9 Drawing Sheets

INSTRUMENT SYSTEM FOR PREPARING A DISC SPACE BETWEEN ADJACENT VERTEBRAL BODIES TO RECEIVE A REPAIR DEVICE

This application claims the benefit of U.S. Provisional Application No. 60/259,262 filed Dec. 29, 2000.

FIELD OF THE INVENTION

The present invention relates to instruments and instrument systems for preparing a disc space between adjacent vertebral bodies in a manner that restores the natural lordosis of the lumbar and cervical spine, so that a repair device can be inserted therein.

BACKGROUND OF THE INVENTION

A large segment of the population have chronic back problems which cause pain and disability. The cause of back pain is often the result of diseased disc material between opposing vertebrae. The diseased disc material usually causes pain because the disc material inadequately supports the opposing vertebrae, thereby allowing the space between the vertebrae to collapse and irritate or damage spinal nerves.

Surgical techniques have been developed to eliminate the persistent pain resulting from diseased disc material. In such techniques, the diseased disc material is removed and the joint between opposing vertebral bodies is fused. Fusion specifically involves removing the diseased disc, preparing a bore for receiving an implant, and inserting the implant between the opposing vertebral bodies.

Spinal fusion implants and the surgical instruments used for implanting these fusion implants are well known in the art. The surgical instruments required for preparing the disc space typically include one or more distractors, drills, reamers, and other instruments.

These prior art instrument sets typically prepare a cylindrical contact area for the fusion implant or artificial disc. Such an instrument set is described in U.S. Pat. No. 5,505,732, to Michelson. The use of a cylindrical shape within the disc space does not restore the natural lordosis of the lumbar and cervical spine, but instead, undesirably establishes a relative kyphosis.

Accordingly, an instrument system is needed for preparing a disc space between adjacent vertebral bodies in a manner that restores the natural lordosis of the lumbar and cervical spine, so that a repair device can be inserted therein.

SUMMARY OF THE INVENTION

An instrument system is described herein for preparing a disc space between adjacent vertebral bodies to receive an implant. The instrument system comprises at least one distractor including a tapered body section for distracting the vertebral bodies in a manner that restores natural lordosis of the lumbar and cervical spines.

One exemplary embodiment of the present invention further comprises a vertebrae immobilizing template. The template is constructed as a sleeve member that can be placed about the distractor when the distractor is inserted into the disc space, to fix the positions of the bodies.

In another exemplary embodiment of the invention, the instrument system further comprises a handle including a coupling member for coupling the handle to the distractor or the template. The handle is useable with the distractor for distracting the disc space and is further useable for placing the template about the distractor after it has been used to distract the vertebral bodies. The handle may include an impaction member for impacting prongs of the template into the distracted vertebral bodies.

In still another exemplary embodiment of the invention, the instrument system further comprises a reamer having a surface with cutting elements for cutting tissue from endplates of the vertebral bodies, and preferably a surface that defines a tapered profile wherein the cutting elements simultaneously cut tissue from opposing endplates of the adjacent vertebral bodies.

BRIEF DESCRIPTION OF THE DRAWINGS

The advantages, nature, and various additional features of the invention will appear more fully upon consideration of the illustrative embodiments now to be described in detail in connection with accompanying drawings where like numerals are used to identify like elements and wherein.

It should be understood that the drawings are for purposes of illustrating the concepts of the invention and are not necessarily to scale.

DETAILED DESCRIPTION OF THE INVENTION

Figure 2A:
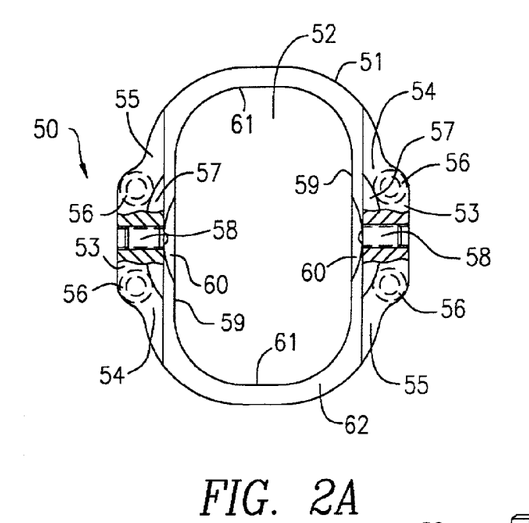
FIG. 2A is an anterior end view of the vertebrae immobilizing template made according an exemplary embodiment of the present invention.
Figure 2B:
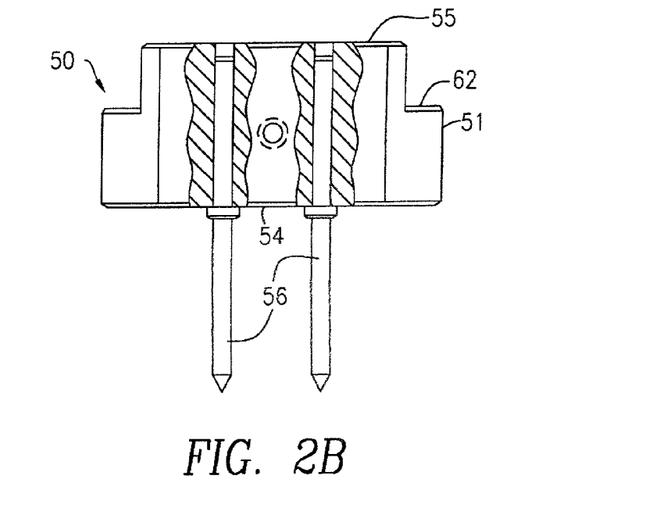
FIG. 2B is a plan view of the template of FIG. 2A.
Figure 2C:
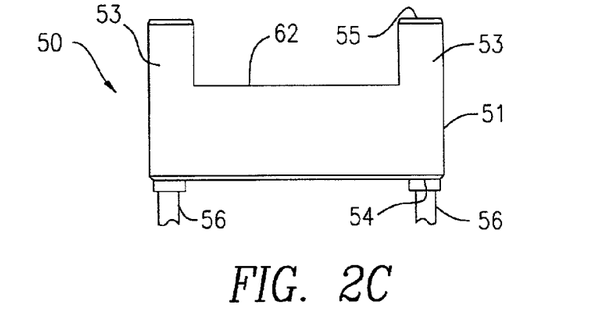
FIG. 2C is an elevational view of the template of FIG. 2A.
Figures 3A, 3B:
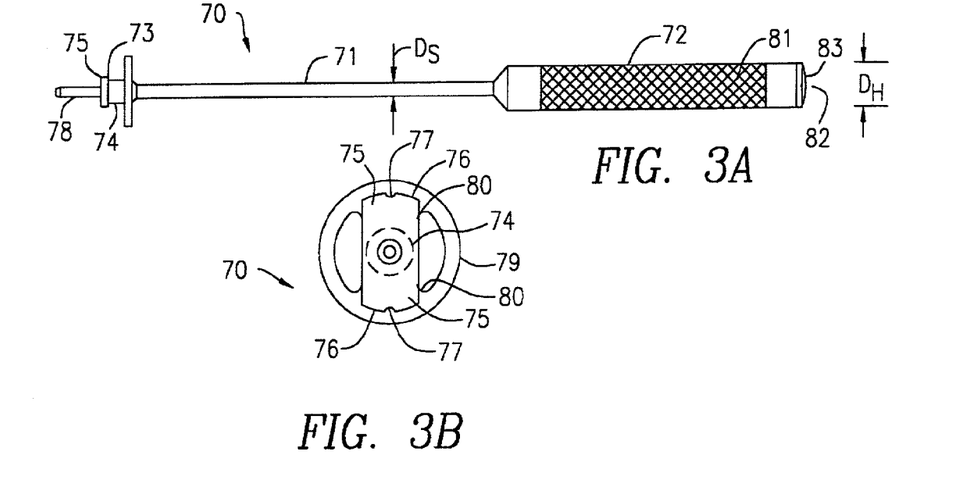
FIG. 3A is a side view of a distractor/template handle made according to an exemplary embodiment of the present invention.
FIG. 3B is a distal end view of the handle of FIG. 3A.
Figure 4A:
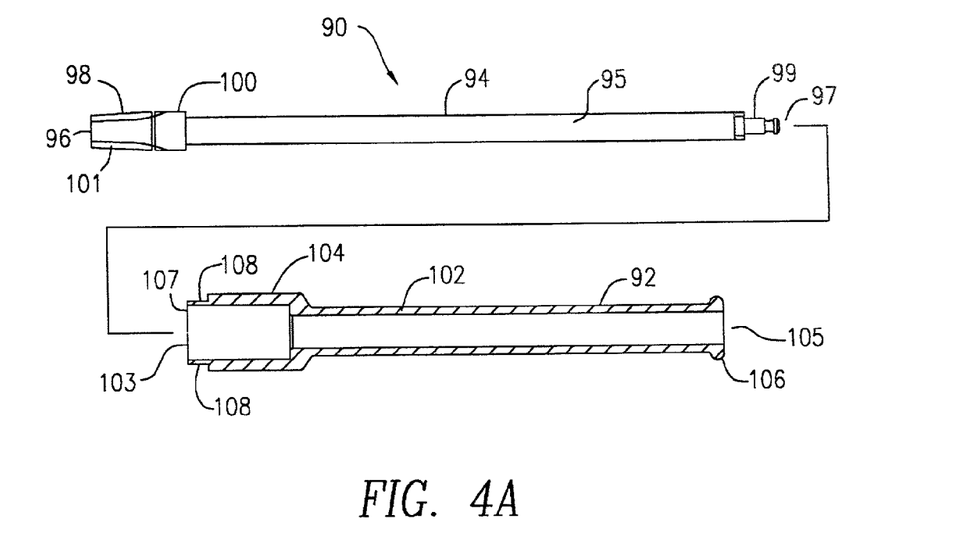
FIG. 4A is an exploded view a reamer assembly made according to an exemplary embodiment of the present invention.

The present invention is an instrument system for preparing a disc space between adjacent vertebral bodies to restore the natural lordosis of the lumbar and cervical spine, so that a repair device of the type which prevents motion between the two adjacent vertebrae (commonly referred to as a fusion implant), or which permits motion between the two adjacent vertebral bodies (sometimes referred to as an artificial disc or artificial motion segment) can be inserted therein. The instrument system may comprise the following instruments: a series of distractors, one of which is shown in FIGS. 1A–1C (denoted by reference character 10), a vertebrae immobilizing template 50 as shown in FIGS. 2A–2C, a distractor/template handle 70 as shown in FIGS. 3A and 3B, and a reamer assembly as shown in FIG. 4.

The series of distractors are used for determining the appropriate size of the repair device to be finally inserted in the disc space, as the distractors are each dimensioned to approximately match a correspondingly dimensioned repair device. Once a distractor has been selected, it is placed into the subject disc space between two adjacent vertebral bodies to distract the bodies. As one of ordinary skill in the art will appreciate, each of the distractors in the series is constructed to provide a certain amount of interdiscal distraction that restores the natural lordosis of the lumbar and cervical spine.

Figure 1A:
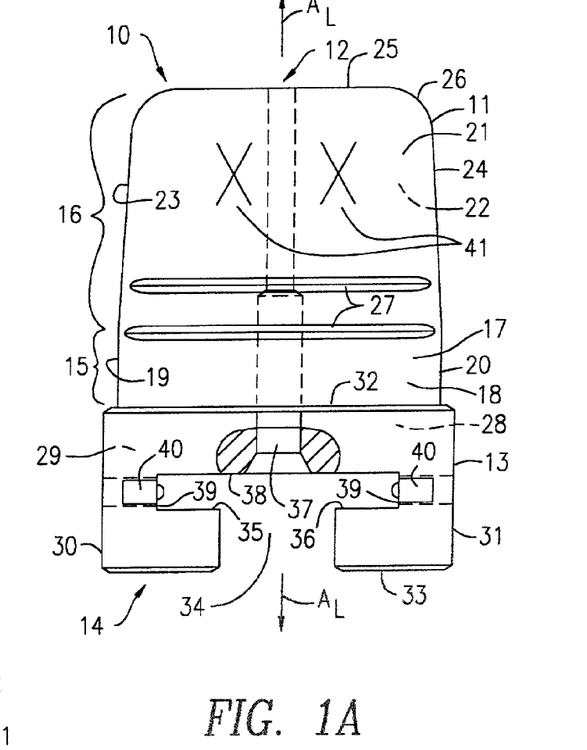
FIG. 1A is a plan view of a distractor made according an exemplary embodiment of the present invention.
Figure 1B:
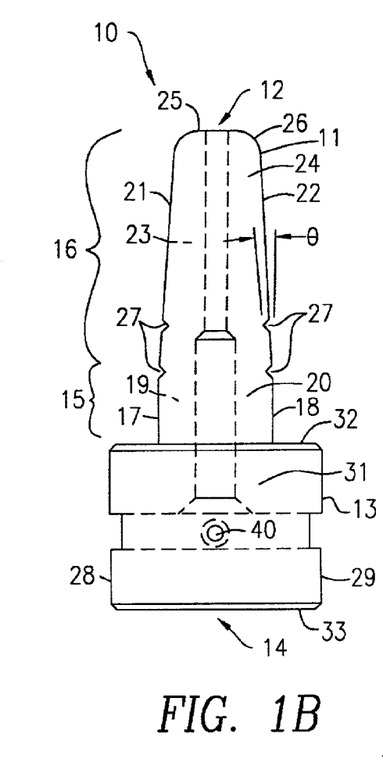
FIG. 1B is an elevational view of the distractor of FIG. 1A.
Figure 1C:
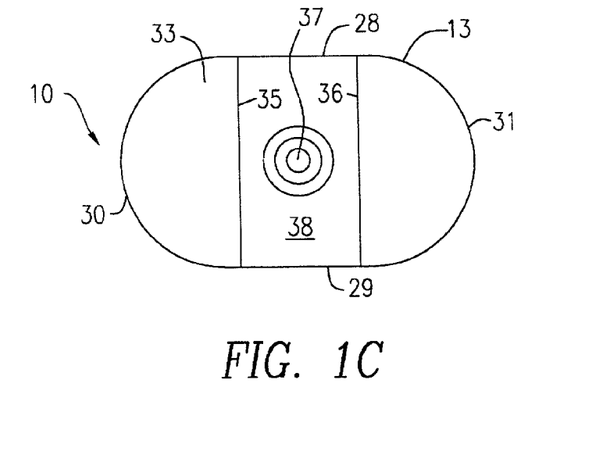
FIG. 1C is an anterior end view of the distractor of FIG. 1A.

Referring collectively to FIGS. 1A–1C, each distractor 10 generally comprises a body section 11 forming an posterior end 12 of the distractor 10 and a connector section 13 forming an anterior end 14 of the distractor 10. The body section 11 includes a base portion 15 and a tapered portion 16. The base portion 15 is formed by parallel superior and inferior wall portions 17, 18 separated by parallel side wall portions 19, 20. The tapered portion 16 defines posterior converging superior and inferior wall portions 21, 22 that respectively extend from the parallel superior and inferior wall portions 17, 18, and posterior converging side wall portions 23, 24 that respectively extend from the parallel side wall portions 19, 20. The posterior converging superior, inferior, and side wall portions 21, 22, 23, 24 meet at a posterior wall 25. The edges 26 where the posterior converging superior, inferior, and side wall portions 21, 22, 23, 24 meet the posterior wall 25 may be radiused.

The posterior converging superior and/or inferior wall portions 21, 22 of the tapered body portion 16, adjacent the base body portion 15, may include one or more groove-like elements 27. The groove-like elements 27 may extend across the posterior converging superior and/or inferior wall portions 21, 22 in a direction which is generally perpendicular to the longitudinal axis $A_L$ of the distractor 10. The posterior converging superior and/or inferior wall portions 21, 22 may also include indicia 41 to indicate height, and/or cross-sectional size.

Figure 1D:
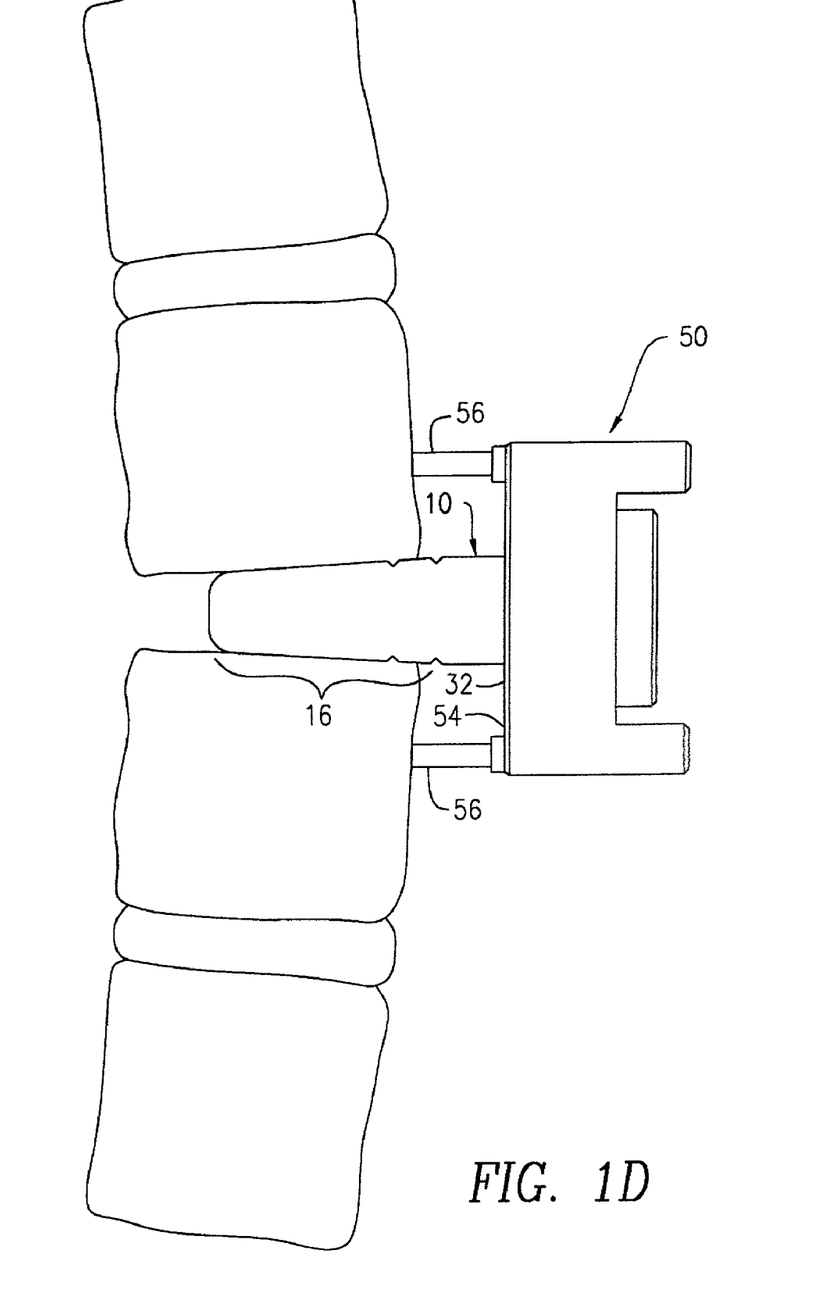
FIG. 1D is a side view of the distractor inserted in the disc space after distraction and a vertebrae immobilizing template fixing the positions of the distracted vertebral bodies.

The posterior converging superior and inferior wall portions 21, 22 define a taper angle θ which matches the tapered portion 16 of the body section 11 to the implant lordosis. In one exemplary embodiment, the taper angle θ defined by the posterior converging superior and inferior wall portions 21, 22, may be about 7 degrees. It should be understood, however, that other taper angles θ may be utilized, depending upon the implant lordosis and the natural lordosis of the disc space being operated on. Lordosis requires that the anterior height of the disc space be greater than the posterior height. As shown in FIG. 1D, the tapered body portion 16 of the distractor 10 reestablishes such a disc space, and prepares a broad contact area for the repair device. The contact area provided by the distractors 10 of the present invention is unlike the disc space resulting from prior art distractors.

Referring still to FIGS. 1A–1C, the connector section 13 of the distractor 10 detachably couples the distractor/template handle 70 to the distractor 10 in a secure manner and aligns the template 50 with the distractor 10. By way of example but not limitation, the connector section 13, when viewed from its anterior end 14 as shown in FIG. 1C, has an elongated configuration formed by superior and inferior wall portions 28, 29 that merge into curved side wall portions 30, 31. The superior, inferior, and side wall portions 28, 29, 30, 31 extend between a posterior flange wall 32 and a generally planar anterior wall 33. The connector section further includes a female coupling member formed by a T-shape slot 34. The T-shaped slot 34 defines inwardly facing locking flanges 35, 36 which cooperate with a correspondingly shaped male coupling member 73 disposed at the marginal distal end of distractor/template handle 70 to provide a bayonet coupling of the handle 70 to the distractor 10. A chamfered pilot pin receiving bore 37 extends from surface 38 of the slot 34 and terminates in the body section 11 of the distractor 10. The pilot pin receiving bore 37 is dimensioned to removably receive a pilot pin 78 formed at a distal-most end of the distractor/template handle 70. The pilot pin 78/pilot pin bore 37 arrangement aids in aligning the male coupling member 73 of the handle 70 with the anterior opening of connector section slot 34 of the distractor 10. Once properly aligned, the coupling member 73 can then be inserted into the slot 34 and rotated (about 90 degrees) to engage the locking flanges 35, 36. To prevent inadvertent relative rotation between the handle 70 and the distractor 10, which would uncouple the handle 70 from the distractor 10, one or more detent elements 40 are provided on surface(s) 39 of the slot 34. The detent elements 40 coact with a corresponding detent element(s) 77 formed on the male coupling member 73 of the handle 70. In one exemplary embodiment, the detent element(s) 40 provided in the slot 34 may be spring-biased ball detent assemblies and the detent element(s) 77 formed on the male coupling member 73 may be indents.

Referring collectively to FIGS. 2A–2C, the vertebrae immobilizing template 50 comprises an elongated sleeve member 51, which defines a reamer sleeve abutment surface 62 and an elongated opening 52 that generally corresponds to the elongated configuration of the connector sections 13 of the distractors 10. The sleeve member opening 52 is dimensioned and configured so that the template 50 can be placed about any of the distractors 10 and is typically sized according to the cross-sectional size of the repair device to be used as will be explained further on. The sleeve member opening 52 defines opposing inner superior/inferior surfaces 59 and opposing side inner surfaces 61. Prong mounting ears 53 are formed on opposing sides of the sleeve member 51. Each mounting ear 53 includes an posterior surface 54 and an anterior surface 55. Spaced-apart prongs 56 extend from the posterior surface 54 of the mounting ears 53. The anterior surface 55 of each prong mounting ear 53 includes a handle impaction recess 57. The inner surfaces 59 of the sleeve member opening 52 include recesses 60 that receive the opposing arms 75 of the male coupling member 73 of the handle 70. One or more detent elements 58 are disposed on the inner surface(s) 59 of the sleeve member opening 52. The detent elements 40 coact with the earlier described detent element(s) 77 of the male coupling member 73 of the handle, to couple the handle 70 to the template 50. In one exemplary embodiment, the detent element(s) 58 may be spring-biased ball detent assemblies.

The vertebrae immobilizing template 50 is placed about the distractor 10 after distraction without removing the distractor 10 from the disc space, and the prongs 56 thereof are impacted into the distracted adjacent vertebral bodies to fix the positions. The prongs 56 of the template 50 are impacted such that the mounting ear posterior surfaces 54 of the template 50 are approximately aligned in the same plane with the posterior flange wall 32 of the distractor 10 as shown in FIG. 1D. This positions the chuck stop 106 provided on a proximal end 97 of a reamer sleeve 92 of the reamer assembly 90 (FIG. 4A) to be described further on, at a fixed distance from where the posterior wall 25 of the distractor 10 was located in the disc space, prior to removal of the distractor 10 from the disc space. With an appropriate length reamer 94 of the reamer assembly 90, this ensures that the reamer 94 will not cut posterior of the position of the posterior wall 25 of the distractor 10. The appropriate length reamer 94 can be determined from the following mathematical relationship:

$$RL-SL=DL+TL$$

where RL is the length of the reamer 94 (not including the chuck-shaft 99), SL is the length of the reamer sleeve 92, DL is the length of the distractor 10 between the posterior wall 25 and the posterior flange wall 32, and TL is the length of the template 50 between the reamer sleeve abutment surface 62 and the mounting ear posterior surfaces 54. Accordingly, the template 50 advantageously enables the reamer assembly 90 to be oriented to the final position of the distractor 10. This is valuable in that fluoroscopic assessment is only required for positioning the distractor 10, thus, minimizing time and x-ray exposures in the operating room. This can be advantageously accomplished without removing the distractor 10 from the disc space. The template 50 is then used for guiding the reamer assembly.

As collectively shown in FIGS. 3A and 3B, the handle 70 is used for inserting a distractor 10 between the vertebral bodies and tapping the distractor 10 into the disc space to distract the bodies. The handle 70 is also used for removing the distractor 10 from the disc space. Additionally, the handle 70 is used for placing the template 50 about the distractor 10 while it is disposed in the disc space, and impacting the prongs 56 of the vertebrae immobilizing template 50 into the distracted adjacent vertebral bodies. The handle 70 typically includes an elongated driver shaft 71 and a handle grip 72 having a diameter $D_H$ which may be greater than the diameter $D_s$ of the shaft 71. Disposed at the distal end of the shaft 71 is the earlier described male coupling member 73. The male coupling member 73 may be a T-shape element formed by a cylindrical body 74 and the earlier described opposing arms 75, the ends of which define arcuate end surfaces 76. The end surfaces 76 include the corresponding detent elements 77 which may be indents as described earlier, that are capable of coacting with the detent elements 40, 58 of the distractors 10 and the template 50. The pilot pin 78 described earlier extends from the male coupling member 73 to define the distal-most end of the handle 70. The edge of the pilot pin 78 may be beveled to aid insertion into the pilot pin receiving bore 37 of the distractor 10. An annular impaction member 79 is disposed at the base of the male coupling member body 74 and is attached thereto by spokes 80. The impaction member 79 engages the handle impaction recesses 57 in the anterior surface 55 of each prong mounting ear 53 of the vertebrae immobilizing template 50.

The handle grip 70 may be provided with a knurled surface 81 or other means for facilitating secure manual gripping of the handle 70. A proximal end 82 of the handle grip 81 is typically provided with a convex surface 83 against which a mallet or other like device may be used to tap the handle 70.

The reamer assembly 90 shown in FIG. 4A, comprises an elongated reamer sleeve 92 and a series of differently dimensioned or sized reamers 94 (only one is shown). Each reamer 94 includes a shaft-like body 95 having a frustoconical end-mill 98 defined at a distal end 96 thereof and a chuck-shaft 99 defined at a proximal end 97 thereof. A cylindrical stop member 100 is disposed proximally to the end-mill 98 on the body 95. The chuck-shaft 99 enables the reamer 94 to be mounted in a chuck 110 of a reamer rotating device 109, such as a drill. The frustoconical end-mill 98 has a tapered profile that approximately matches the taper angle θ of the distractors 10. The exterior surface of the frustoconical end-mill 98 typically includes a plurality of bone cutting elements 101 for cutting tissue from the opposing endplates of the distracted vertebral bodies. The bone cutting elements 101 may be configured, in one exemplary embodiment, as longitudinal flutes. This construction enables the reamer 94 to simultaneously prepare the opposing endplates of the distracted adjacent vertebral bodies as it is passed across the endplates. The end-mills 98 of the reamers 94 are each sized so as to controllably remove a specified amount of tissue off of the opposing endplates of the vertebral bodies. The size of each reamer end-mill 98 corresponds to the size of a corresponding distractor 10. Thus, the particular reamer 94 selected for preparing the endplates is based on the distractor 10 selected for distraction. Nonlinear geometries can be accommodated through modifications to the shape of template 50 and reamer end-mill 98.

The sleeve 92 includes a cylindrical body 102 that is dimensioned to rotatively receive the reamers 94. The cylindrical body 102 includes an enlarged cylindrical section 104 at a distal end 103 thereof and a chuck stop 106 at a proximal end 105 thereof.

Figures 4B, 4C:
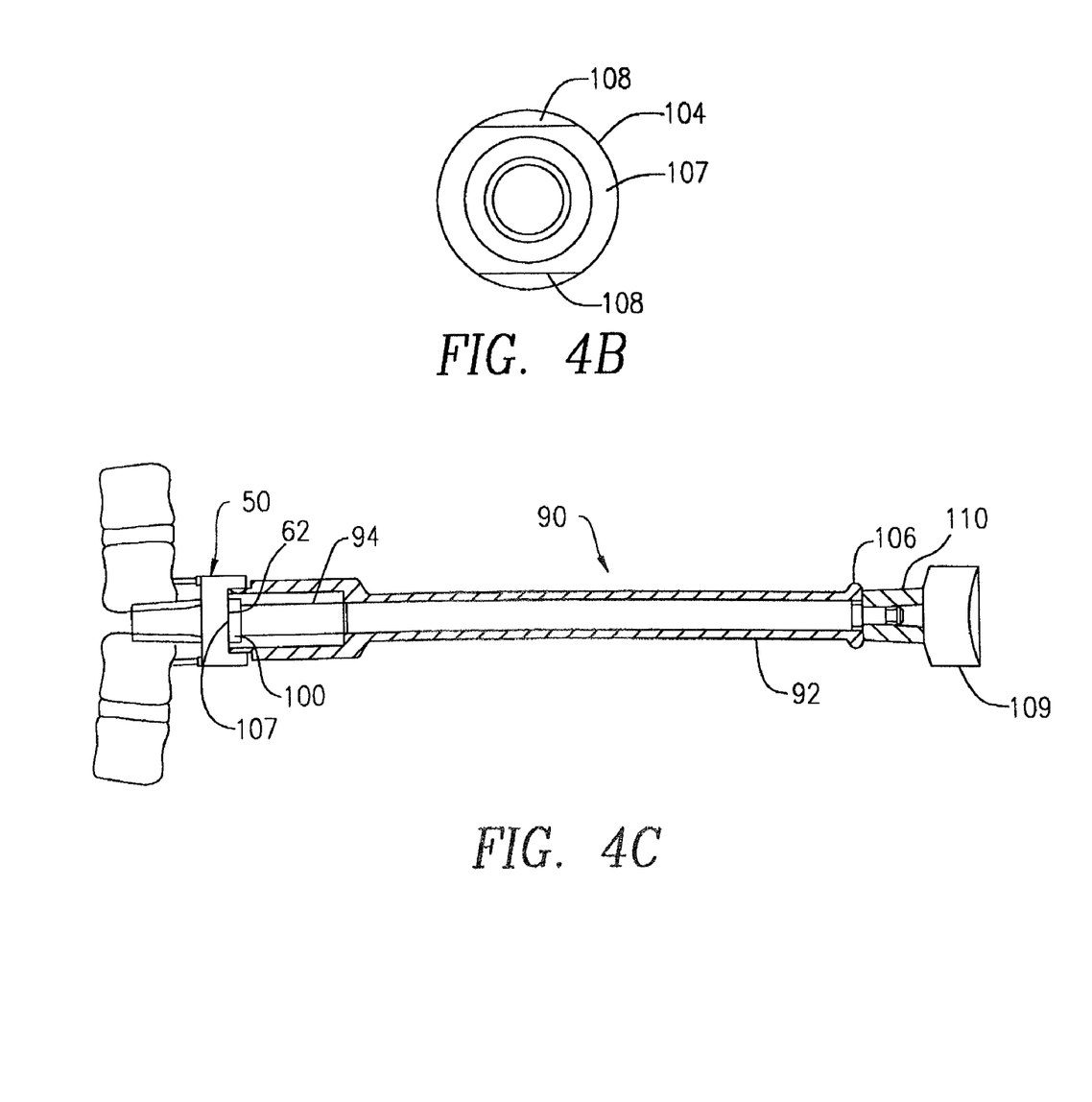
FIG. 4B is a distal end view of a reamer sleeve of the reamer assembly of FIG. 4A.
FIG. 4C is a side view of the reamer assembly depicting its use with the vertebrae immobilizing template, wherein the reamer sleeve is shown engaged with the vertebrae immobilizing template, and a reamer of the reamer assembly is shown disposed in the disc space and cutting the endplates of the vertebral bodies.

As best shown in FIG. 4B, the enlarged cylindrical section 104 includes a distal edge surface 107 for engaging the reamer sleeve abutment surface 62 of the template 50. The distal edge surface 107 includes reliefs 108 for clearing the mounting ears 53 of the template 50.

As shown in FIG. 4C, the sleeve 92 operates to limit the depth of the reamer 94 travel into the disc space as the chuck 110 of the reamer rotating device 109 contacts the chuck stop 106 of the reamer sleeve 92. Side-to-side travel of the reamer 94 is limited by the cylindrical stop 100 on the reamer 94, which engages the opposing side inner surfaces 61 of the template 50.

The instruments 10, 50, 70, 90 of the system are typically made from stainless steel. One of ordinary skill in the art will of course appreciate that one or more of the instruments 10, 50, 70, 90 may be made from any other suitable biocompatible material.

The following surgical technique, known in the art as an anterior inter-body fusion, illustrates the interaction of the instruments 10, 50, 70, 90 of the instrument system of the present invention as used in the implantation of an exemplary fusion device, such as an alif device constructed from HEDROCEL®, which is available from Implex Corporation.

Preoperatively, the surgeon must decide which intervertebral levels to fuse. This may be done using a variety of diagnostic techniques, such as radiographs, MRI, discography, patient history, and physical examination.

For the L5/S1 level, the patient is positioned in the supine position, with a pad under the lumbar spine to maintain lordosis. For higher levels, the surgeon may choose either a supine position or a lateral decubitus position. In either case, a table should be used that accommodates both lateral and anterior-posterior radiographs.

A vascular or general surgeon usually provides the exposure while the spine surgeon assists and then performs the fusion. To access the L5/S1 level, the lumbar spine is exposed through a low transverse or paramedian incision while a retroperitoneal plane is developed. For higher levels, it may be more appropriate to use a midaxillary incision aligned over the level to be treated.

The device(s) are implanted in an anterior-posterior direction so that the retroperitoneal plane must be developed from the anterior direction.

Standard general and/or vascular surgical instruments are used to perform the exposure down to the level(s) of the fusion. They are also used to maintain the exposure via the appropriate retractors.

The exposure is completed when the anterior surface of the spine is exposed.

To identify the correct disc level(s) and that the approach is in the appropriate place, needle(s) are inserted into the intervertebral disc as markers, and the location(s) determined by means of a C-arm anterior-posterior radiograph. If the needle is not along the midline, it should be repositioned and an additional radiograph taken to assure its proper location.

Iliac crest autograft is harvested from the iliac crest. This can be done using standard techniques. Depending on the size and height of the device used, approximately 0.5 to 1.5 cc$^3$ of bone is required at each fusion level. The bone graft does not provide structural support but instead is used for its biological properties to stimulate bone formation.

An annulotomy is performed using a scalpel to make a window in the annulus. It should be centered about the midline. It should be as long as the space to be occupied by the implant(s).

Pituitary rongeurs and small curettes can be used to perform the discectomy.

Based on radiographic evaluation, an initial distractor 10 is selected. It is assembled to the handle 70. The pilot pin 78 on the handle 70 fits within a receiving bore 37 on the anterior surface 38 of the distractor 10. The handle 70 is rotated to align the male coupling member 73 of the handle 70 with the slot 34 in the connector section 13 of the distractor 10. The handle 70 is advanced until the pilot pin 78 is fully engaged. The handle 70 is rotated 90 degrees to engage the ball detents 40 that help hold the handle 70 in place relative to the distractor 10.

Figure 5:
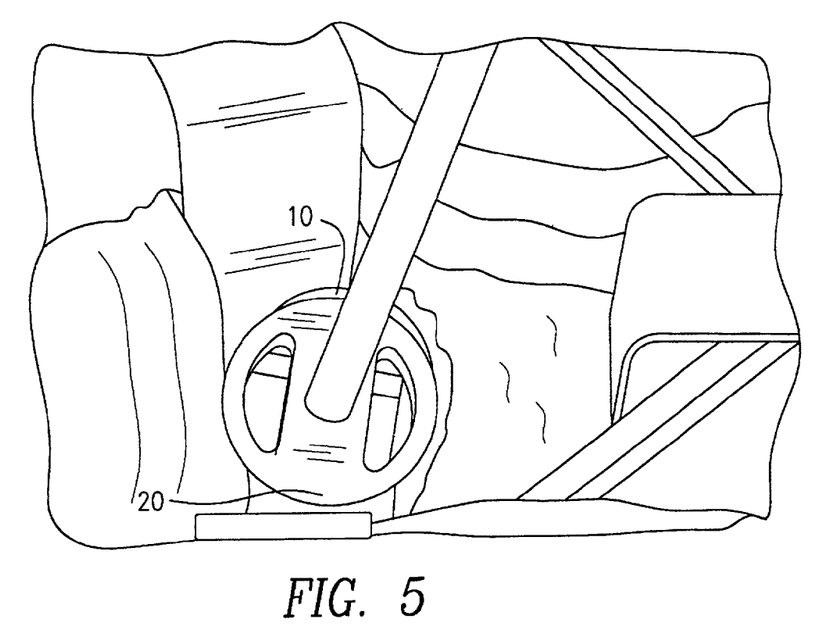
FIGS. 5–12 depict an exemplary method of using the instrument system of the present invention.

As shown in FIG. 5, the distractor 10 is placed into the interdiscal space, using the handle 70 to manipulate it. The distractor 10 is inserted under intermittent lateral fluoroscopic/radiographic evaluation until the distractor 10 is appropriately seated posteriorly, a few millimeters anterior of the posterior border of the body.

Figure 6:
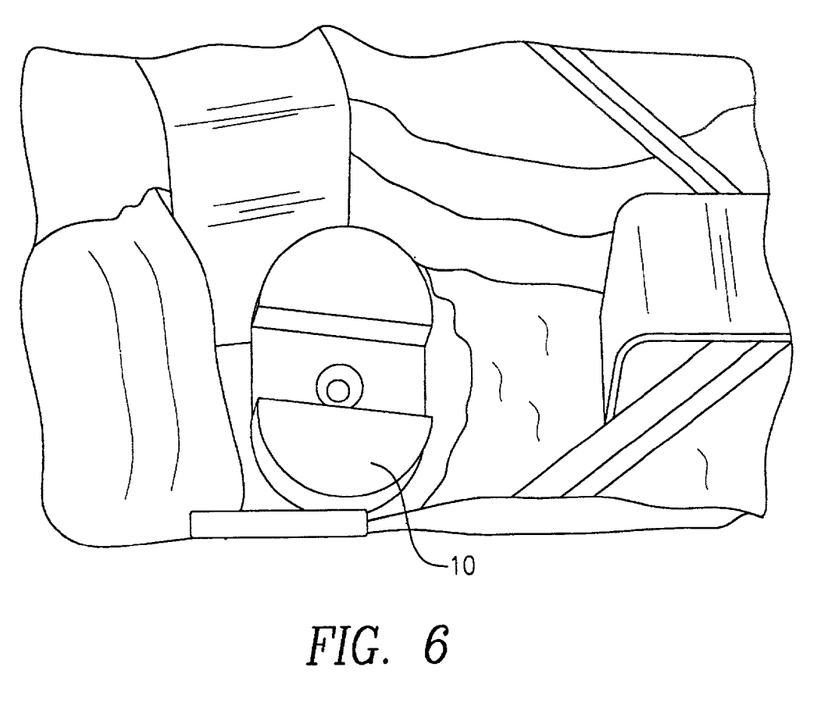

The distractors 10 are changed until the appropriate height of the distractor 10 is determined. The height of the distractor 10 is appropriate when the annulus is fully tensioned. Tensioning is checked by fully seating a distractor 10 and then pulling on the handle 70 to remove it. When the distractor 10 disengages easily, a larger distractor 10 should be placed. When the appropriate distractor 10 is determined and in place, the handle 70 is removed as shown in FIG. 6.

Once the distractor 10 is fully seated in the disc space and the handle 70 is removed, the cross sectional size of the device is determined from the grooves 27 on the superior and inferior surfaces 21, 22 of the distractor 10. These grooves 27 are visible from lateral fluoroscopy/radiograph. Each groove 27 corresponds to an implant cross section and to a template 50 size as well.

Figure 7:
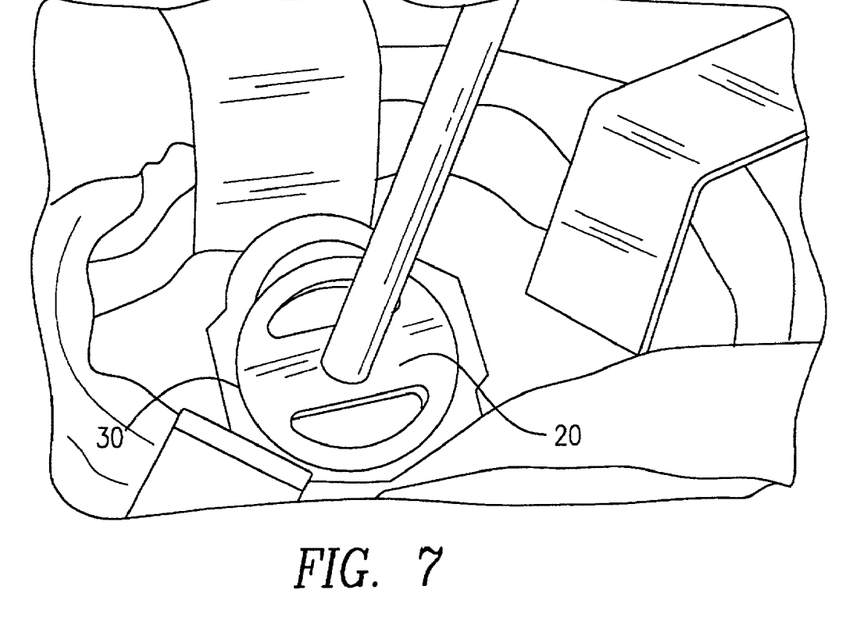

After the appropriate distractor 10 has been placed into the interdiscal space, the handle 70 is assembled to the appropriately sized template 50. Ball detents 58 of the template 50 indicate the appropriate orientation of the handle 70 with respect to the template 50. This assembly is then placed over the distractor 10 and slid into place. As shown in FIG. 7, a mallet is used with the handle 70 to impact the template 50 into the two vertebral bodies. The prongs 56 on the template 50 engage the adjacent vertebral bodies and hold the template 50 in place. Impaction continues until the template 50 bottoms out on the distractor 10. This fixes the position of the template 50 relative to the posterior edge of the distractor 10. The handle 70 is then rotated 90 degrees. The ball detents 40 from the distractor 10 engage the handle 70, indicating the appropriate position. The distractor 10 is then withdrawn, leaving the template 50.

Figure 8:
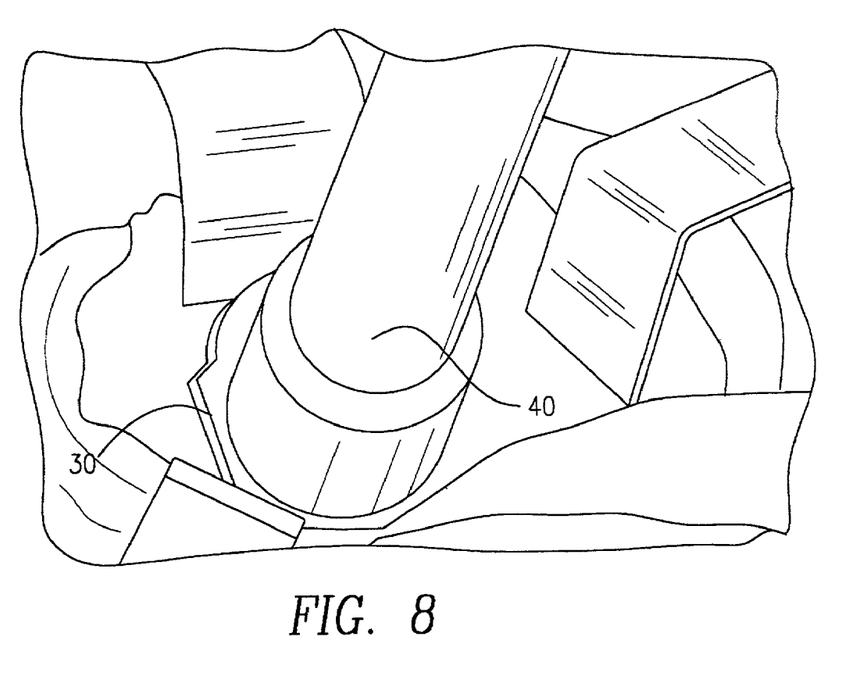
Figure 9:
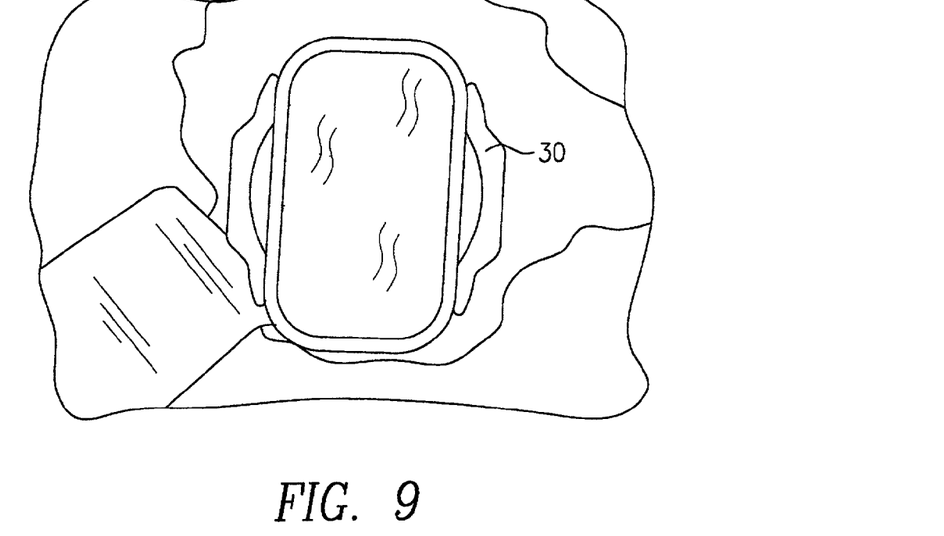

As shown in FIG. 8, the endplates are then prepared using the reamer assembly 90 having an appropriately sized one of the reamers 94 installed in the reamer sleeve 92. The reamer assembly 90 is used to remove a fixed amount of bone off of the endplates, based on the fit of the initial distractor 10. The reamer sleeve 92 prevents the rotation of the reamer 94 from catching adjacent tissue. The sleeve 92 also limits the penetration of the reamer 94 into the disc space as mentioned earlier. The reamer assembly 90 mates with the template 50. The template 50 limits the lateral motion of the reamer assembly 90. The template 50 and reamer assembly 90 result in removal of approximately 1.5 mm from each endplate. The reamer assembly 90 is then removed as shown in FIG. 9.

One Hedrocel ALIF device is used at a single level. The proper implant size is determined by the insertion depth of the distractor 10 and the distractor height used.

Figure 10:
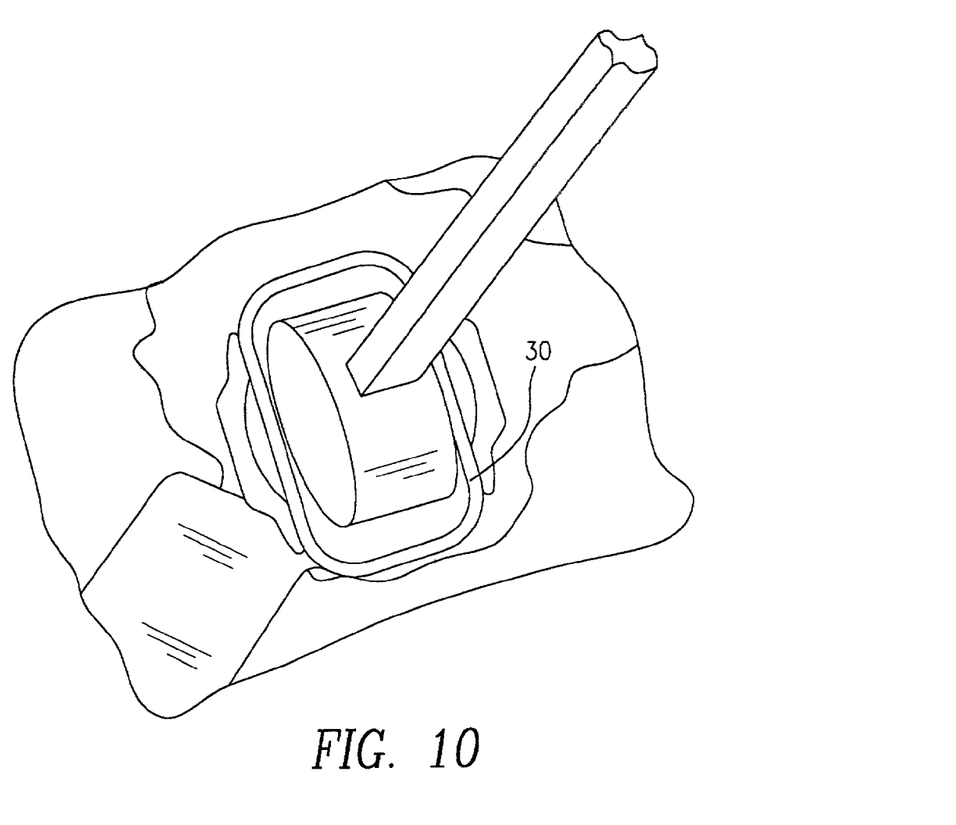
Figure 11:
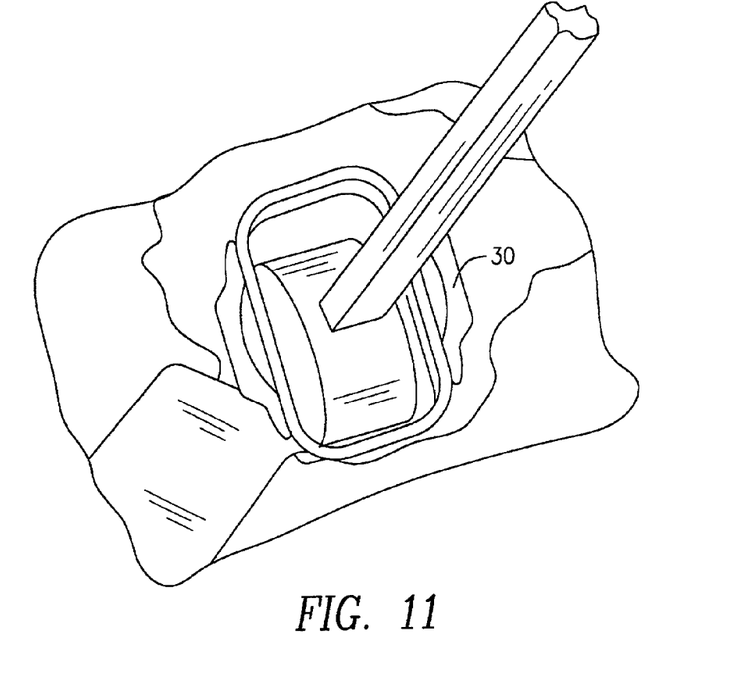

The following steps describe the insertion of a single implant 110. Placement of the implant 120 is typically along the midline. On a sterile table, the hole(s) of the appropriately sized implant 120 is stuffed with the already harvested autologous bone. The implant 120 is then placed on an inserter 121. As shown in FIG. 10, the implant 120 is passed through the template 50, into the space and the inserter 121 removed. The implant 120 is fully seated using a tamp 122 as shown in FIG. 11.

The implant's height is sized so that it will further distract the vertebral bodies by approximately ½ mm beyond the distraction of the initial device.

Figure 12:
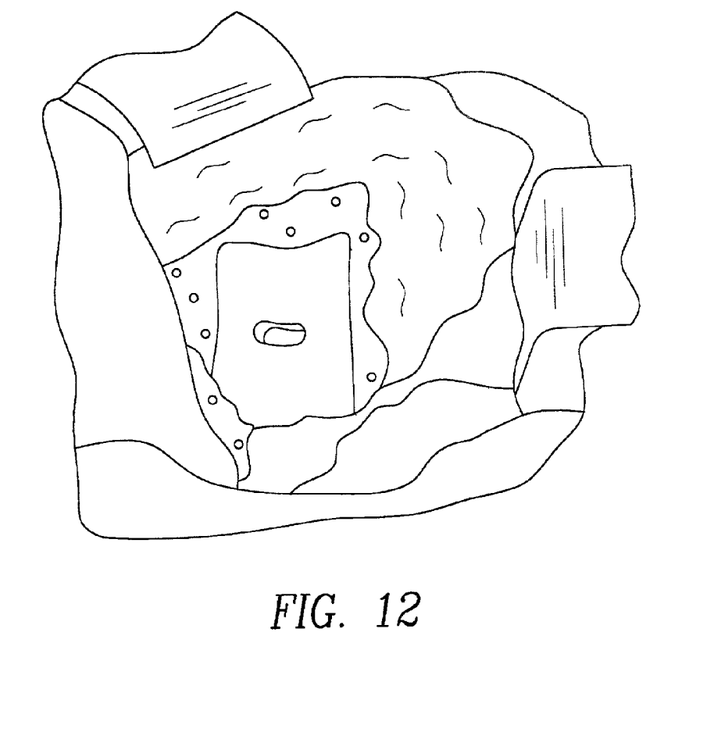

Following final implant insertion, lateral and A/P radiographs may be taken to assure proper implant placement. Once proper placement is assured, the template 50 is removed as shown in FIG. 12, using the handle 70 (not shown).

While the foregoing invention has been described with reference to the above embodiments, various modifications and changes can be made without departing from the spirit of the invention. Accordingly, all such modifications and changes are considered to be within the scope of the appended claims.

What is claimed is:

1. An instrument system for preparing a disc space between adjacent vertebral bodies to receive a repair device, the instrument system comprising:
   at least one distractor including:
   a tapered body section for distracting the vertebral bodies in a manner that restores natural lordosis of the lumbar and cervical spines, the tapered body section formed by:
   an end wall;
   a first pair of opposing wall portions converging toward the end wall; and
   a second pair of opposing wall portions converging toward the end wall; and a connector section opposite the body section, the connector section for coupling a handle to the distractor, the connector section including a detent element; amd a base portion connecting the tapered body section to the connector section;

wherein said tapered body section has a length that is substantially greater than a length of said base portion such that when said distractor is inserted between the adjacent verebral bodies the first pair of opposing wall portions engage the adjacent vertebral bodies to obtain said natural lordosis.

2. The instrument system according to claim 1, wherein the at least one distractor includes a longitudinal axis and at least one of the first pair of wall portions includes a groove that extends generally perpendicular to the longitudinal axis.

3. The instrument system according to claim 1, wherein the at least one distractor includes a longitudinal axis and each of the first pair of wall portions includes a groove that extends generally perpendicular to the longitudinal axis.

4. The instrument system according to claim 1, wherein the connector section includes a female coupling member.

5. The instrument system according to claim 4, wherein the female coupling member is formed by a T-shape slot.

6. The instrument systems according to claim 5, wherein the T-shape slot defines inwardly facing locking flanges.

7. The instrument system according to claim 5, wherein the T-shape slot defines a surface, the surface including a bore for receiving a pilot pin formed at an end of the handle.

8. The instrument system according to claim 1, further comprising indicia for indicating a dimension of the at least one distractor, the indicia provided by at least one of the walls of the first and second pairs of opposing walls.

9. The instrument system according to claim 1, further comprising a vertebrae immobilizing template, the template constructed as a sleeve member that can be placed about the at least one distractor when the at least one distractor is inserted into the disc space, to fix the positions of the bodies.

10. The instrument system according to claim 9, wherein the sleeve member includes opposing prongs extending therefrom for fixing the positions of the vertebral bodies when the prongs are impacted into the bodies.

11. The instrument system according to claim 10, further comprising a reamer assembly including a reamer having a surface with cutting elements for cutting tissue from endplates of the vertebral bodies.

12. The instrument system according to claim 11, wherein the surface of the reamer defines a tapered profile, the cutting elements simultaneously cutting tissue from opposing endplates of the adjacent vertebral bodies.

13. The instrument system according to claim 11, wherein the reamer assembly further includes a reamer sleeve that operates as a stop to limit reamer travel depth into the disc space.

14. The instrument system according to claim 11, wherein the sleeve member of the template includes opposing prongs extending therefrom for fixing the positions of the vertebral bodies when the prongs are impacted into the bodies, the prongs being impacted such that a surface of the template approximately aligns with a surface of the distractor thereby locating the template so that when the reamer assembly is used to cut tissue from endplates of the vertebral bodies, the reamer of the reamer assembly is disposed at a fixed distance from where a posterior wall of the distractor was positioned within the disc space.

15. The instrument system according to claim 11, further comprising a handle including a coupling member for coupling the handle to the at least one distractor or the template, the handle being useable with the at least one distractor for distracting the disc space and being further useable for placing the template about the at least one distractor after it has been used to distract the vertebral bodies.

16. The instrument system according to claim 15, wherein the handle further includes an impaction member for impacting the template.

17. The instrument system according to claim 15, wherein the template includes at least one ball detent extending from a side surface of the sleeve member that cooperates with the coupling member of the handle to couple the handle to the template.

18. The instrument system according to claim 1, further comprising a handle including a coupling member that connects the handle to the at least one distractor, the handle being useable with the at least one distractor for distracting the vertebral bodies.

19. The instrument system according to claim 1, further comprising a reamer having a surface with cutting elements for cutting tissue from endplates of the vertebral bodies.

20. The instrument system according to claim 1, wherein the at least one distractor further includes a connector section opposite the body section, the connector section for coupling a handle to the at least one distractor.

21. The instrument system according to claim 20, wherein the connector section includes at least one ball detent for use in coupling the handle to the at least one distractor.

22. A distractor for use in a system that prepares a disc space between adjacent vertebral bodies to receive a repair device, the distractor comprising:

a tapered body section for distracting the vertebral bodies in a manner that restores natural lordosis of the lumbar and cervical spines, the tapered body section formed by:

an end wall;

a first pair of opposing wall portions converging toward the end wall; and a second pair of opposing wall portions converging toward the end wall; and a connector section opposite the body section, the connector section for coupling a handle to the distractor, the connector section including a detent element;

a connector section opposite the body section, the connector section for coupling a handle to the distractor, the connector section including a detent element; and a base portion connecting the tapered body section to the connector section;

wherein said tapered body section has a length that is substantially greater than a length of said base portion such that when said distractor is inserted between the adjacent vertebral bodies the first pair of opposing wall portions engage the adjacent vertebral bodies to obtain said natural lordosis.

23. The distractor according to claim 22, wherein the connector section includes a female coupling member.

24. The distractor according to claim 23, wherein the female coupling member is formed by a T-shape slot.

25. The distractor according to claim 24, wherein the T-shape slot is defined by inwardly facing locking flanges.

26. The distractor according to claim 25, wherein the T-shape slot is further defined by a surface, the surface including a bore for receiving a pilot pin formed at an end of the handle.

27. The distractor according to claim 22, further including a longitudinal axis, wherein at least one of the first pair of wall portions includes a groove that extends generally perpendicular to the longitudinal axis.

28. The distractor according to claim 22, further including a longitudinal axis, wherein each of the first pair of wall portions includes a groove that extends generally perpendicular to the longitudinal axis.

29. The distractor according to claim 22, further comprising indicia for indicating a dimension of the distractor, the indicia provided by at least one of the walls of the first and second pair of opposing walls.

* * * * *